US012685763B2

(12) United States Patent　　　(10) Patent No.:　US 12,685,763 B2
Yue　　　　　　　　　　　　　　　　　(45) Date of Patent:　　Jul. 21, 2026

(54) METHODS FOR TREATING INTRACRANIAL HEMORRHAGE AND ASSESSING EFFICACY

(71) Applicant: Alexion Pharmaceuticals, Inc., Boston, MA (US)

(72) Inventor: Patrick Yue, South San Francisco, CA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 1084 days.

(21) Appl. No.: 17/428,804

(22) PCT Filed: Feb. 7, 2020

(86) PCT No.: PCT/US2020/017165
　　§ 371 (c)(1),
　　(2) Date: Aug. 5, 2021

(87) PCT Pub. No.: WO2020/163685
　　PCT Pub. Date: Aug. 13, 2020

(65) Prior Publication Data
　　US 2022/0125894 A1　　　Apr. 28, 2022

Related U.S. Application Data

(60) Provisional application No. 62/802,645, filed on Feb. 7, 2019.

(51) Int. Cl.
| | |
|---|---|
| *A61K 38/36* | (2006.01) |
| *A61K 31/444* | (2006.01) |
| *A61K 31/4545* | (2006.01) |
| *A61K 31/5355* | (2006.01) |
| *A61K 31/727* | (2006.01) |
| *A61K 38/00* | (2006.01) |
| *A61K 38/48* | (2006.01) |
| *A61P 7/04* | (2006.01) |
| *G01N 33/86* | (2006.01) |

(52) U.S. Cl.
　　CPC ........ *A61K 38/4846* (2013.01); *A61K 31/444* (2013.01); *A61K 31/4545* (2013.01); *A61K 31/5355* (2013.01); *A61K 31/727* (2013.01); *A61P 7/04* (2018.01); *C12Y 304/21006* (2013.01); *G01N 33/86* (2013.01); *G01N 2333/96444* (2013.01)

(58) Field of Classification Search
　　CPC .... A61K 38/4846; A61K 38/36; A61K 38/00; A61K 2300/00; A61K 31/444; A61K 31/4545; A61K 31/5355; A61K 31/727;

A61P 7/04; C12N 9/6432; C12Y 304/21006; G01N 2333/96444; G01N 2800/2871; G01N 2800/52; G01N 33/86
See application file for complete search history.

(56) References Cited

U.S. PATENT DOCUMENTS

| | | | |
|---|---|---|---|
| 2003/0064414 A1 | 4/2003 | Benecky et al. | |
| 2009/0098119 A1* | 4/2009 | Lu ............................ | A61P 7/04 |
| | | | 435/69.6 |
| 2015/0343034 A1 | 12/2015 | Pittman et al. | |
| 2018/0236049 A1 | 8/2018 | Sinha et al. | |

FOREIGN PATENT DOCUMENTS

| | | |
|---|---|---|
| WO | WO 2009/042962 A2 | 4/2009 |
| WO | WO 2017/197332 | 11/2017 |
| WO | WO 2018/115235 | 6/2018 |

OTHER PUBLICATIONS

Abstracts Presented at the Neurocritical Care Society (NCS) 16th Annual Meeting. Neurocritical Care. Springer US, New York. Sep. 2018; vol. 29, No. Suppl 1, pp. 2-363.
Connolly, et al. Andexanet alfa for acute major bleeding associated with factor Xa inhibitors. New England Journal of Medicine. Sep. 22, 2016; 375(12):1131-1141.
Connolly, et al. Andexanet alfa for acute major bleeding associated with factor Xa inhibitors. Journal of Vascular Surgery. Jan. 2017; 65:279-280.
Extended European Search Report and Opinion dated Oct. 31, 2022 for EP Application No. 20752610.4. 9 pages.
International Search Report and Written Opinion for PCT/US2020/017165 dated Jun. 9, 2020, 16 pages.
Baker. Coagulation Factor Xa (Recombinant), Inactivated-zhzo (Andexanet Alfa). Hospital Pharmacy. Jul. 15, 2018; 53(5):286-291.

(Continued)

*Primary Examiner* — Julie Ha
(74) *Attorney, Agent, or Firm* — Sheppard Mullin Richter & Hampton LLP

(57) ABSTRACT

Compositions and methods useful for assessing the hemostatic efficacy in a patient having suffered from intracranial hemorrhage while undergoing an anticoagulation treatment with a factor Xa (fXa) inhibitor are described. The method can include administering to the patient a fXa derivative that has reduced catalytic activity as compared to the wild-type fXa protein, is capable of binding to the factor Xa inhibitor and cannot assemble into a prothrombinase complex; obtaining a blood sample from the patient following the administration; and measuring an anti-fXa activity in the sample, wherein the anti-fXa activity reflects the hemostatic efficacy in the patient. Once the assessment is made, suitable medical interventions can be implemented.

7 Claims, 5 Drawing Sheets

Specification includes a Sequence Listing.

(56) References Cited

OTHER PUBLICATIONS

Connolly, et al. Full Study Report of Andexanet Alfa for Bleeding Associated with Factor Xa Inhibitors. New England Journal of Medicine. Feb. 7, 2019; 380(14):1326-1335.

Kaatz, et al. Reversing factor Xa inhibitors—clinical utility of andexanet alfa. Journal of Blood Medicine. Sep. 13, 2017; 8:141-149.

Lu, et al. Andexanet alfa effectively reverses edoxaban anticoagulation effects and associated bleeding in a rabbit acute hemorrhage model. PLoS One. Mar. 28, 2018; 13(3):e0195122.

* cited by examiner

METHODS FOR TREATING INTRACRANIAL HEMORRHAGE AND ASSESSING EFFICACY

CROSS REFERENCE TO RELATED APPLICATIONS

This application is the United States National Phase Application of PCT/US2020/017165, filed Feb. 7, 2020, and claims the benefit under 35 U.S.C. § 119(e) of U.S. Provisional Application Ser. No. 62/802,645, filed Feb. 7, 2019, the content of which is incorporated by reference in its entirety into the present disclosure.

BACKGROUND

Factor Xa inhibitors, e.g., apixaban, rivaroxaban, edoxaban, betrixaban, and enoxaparin, have a positive benefit-risk profile for treatment and prevention of thrombotic events but may cause or worsen acute major bleeding with substantial morbidity and mortality. Factor Xa inhibitor-associated acute major bleeding episodes may be difficult to treat for lack of a specific reversal agent.

Andexanet alfa (coagulation factor Xa [recombinant] inactivated-zhzo) is a modified recombinant inactive form of factor Xa designed specifically to bind and sequester factor Xa inhibitor molecules, thereby rapidly reducing anti-factor Xa activity, a measure of the anticoagulant effect of factor Xa inhibitors. In healthy subjects receiving either apixaban or rivaroxaban, andexanet rapidly reduced both unbound fraction of factor Xa inhibitor and anti-factor Xa activity, with minimal adverse effects.

Monitoring of the hemostatic efficacy following an andexanet treatment can be important, in particular in elderly patients. Such monitoring can provide helpful information for deciding whether a patient is suitable for certain medical procedure and whether additional andexanet is required.

SUMMARY

The present disclosure provides, in one embodiment, methods useful for assessing the hemostatic efficacy in a patient having suffered from intracranial hemorrhage while undergoing an anticoagulation treatment with a factor Xa (fXa) inhibitor.

Such assessment is based on the unexpected discovery that, even though there is no correlation between anti-factor Xa activity and hemostatic efficacy in the general patient population following treatment with andexanet alfa, a good correlation was surprisingly detected in intracranial hemorrhage patients.

Accordingly, in one embodiment, the present disclosure provides a method for assessing the hemostatic efficacy in a patient having suffered from intracranial hemorrhage while undergoing an anticoagulation treatment with a factor Xa (fXa) inhibitor, comprising: administering to the patient a fXa derivative that has a deletion of at least 50% of amino acid residues 6-39 of the light chain and a modification at the active site on the heavy chain, wherein the fXa derivative has reduced catalytic activity as compared to the wild-type fXa protein, and is capable of binding to the factor Xa inhibitor; obtaining a blood sample from the patient following the administration; and measuring an anti-fXa activity in the sample, wherein the anti-fXa activity reflects the hemostatic efficacy in the patient.

In some embodiments, the method further comprises estimating the hemostatic efficacy based on the anti-fXa activity. In some embodiments, the method further comprises measuring the anti-fXa activity in a sample obtained from the patient prior to the administration of the fXa derivative. In some embodiments, the estimation takes as input the anti-fXa activities prior to and following the administration.

In some embodiments, the administration comprises a bolus injection of the fXa derivative. In some embodiments, the administration further comprises an infusion of the fXa derivative after the bolus injection. In some embodiments, the blood sample is obtained at 10 minutes to 4 hours following the administration. In some embodiments, the anti-fXa activity is measured with a chromogenic assay.

In some embodiments, the method further comprises determining, based on the anti-fXa activity, (a) whether to administer to the patient a second dose of the fXa derivative, (b) a likelihood that the patient will suffer from a thrombotic event, (c) a minimum time for monitoring or treatment, or (d) whether a surgical procedure is indicated for the patient.

In some embodiments, the method further comprises administering to the patient a second dose of the fXa derivative if the anti-fXa activity is above a predetermined anti-fXa activity threshold or if the hemostatic efficacy is below a predetermined hemostatic efficacy threshold.

Also provided, in one embodiment, is a method for treating intracranial hemorrhage in a patient undergoing an anticoagulation treatment with a factor Xa (fXa) inhibitor, comprising: administering to the patient a fXa derivative that has a deletion of at least 50% of amino acid residues 6-39 of the light chain and a modification at the active site on the heavy chain, wherein the fXa derivative has reduced catalytic activity as compared to the wild-type fXa protein, and is capable of binding to the factor Xa inhibitor; obtaining a blood sample from the patient following the administration; measuring an anti-fXa activity in the sample; and administering to the patient a second dose of the fXa derivative if the anti-fXa activity is above a predetermined anti-fXa activity threshold.

In some embodiments, the predetermined anti-fXa activity threshold is from 30 to 50 ng/ml when the fXa inhibitor is apixaban, rivaroxaban, betrixaban, or edoxaban, or from 0.25 to 0.5 IU/ml when the fXa inhibitor is enoxaparin.

Another embodiment provides a method for conducting a surgery in a patient having suffered from intracranial hemorrhage while undergoing an anticoagulation treatment with a factor Xa (fXa) inhibitor, comprising: administering to the patient a fXa derivative that has a deletion of at least 50% of amino acid residues 6-39 of the light chain and a modification at the active site on the heavy chain, wherein the fXa derivative has reduced catalytic activity as compared to the wild-type fXa protein, and is capable of binding to the factor Xa inhibitor; obtaining a blood sample from the patient following the administration; measuring an anti-fXa activity in the sample; and conducting the surgery in the patient if the anti-fXa activity is below a predetermined anti-fXa activity threshold or if a hemostatic efficacy estimated based on the anti-fXa activity is above a predetermined hemostatic efficacy threshold.

In some embodiments, the predetermined anti-fXa activity threshold is from 30 to 50 ng/ml when the fXa inhibitor is apixaban, rivaroxaban, betrixaban or edoxaban, or from 0.25 to 0.5 IU/ml when the fXa inhibitor is enoxaparin.

Yet another embodiment provides a method for preventing a thrombotic event in a patient having suffered from intracranial hemorrhage while undergoing an anticoagulation treatment with a factor Xa (fXa) inhibitor, comprising: administering to the patient a fXa derivative that has a deletion of at least 50% of amino acid residues 6-39 of the light chain and a modification at the active site on the heavy chain, wherein the fXa derivative has reduced catalytic activity as compared to the wild-type fXa protein, and is capable of binding to the factor Xa inhibitor; obtaining a blood sample from the patient following the administration; measuring an anti-fXa activity in the sample; determining a likelihood that the patient will suffer from a thrombotic event based on the anti-fXa activity; and administering to the patient an anticoagulation therapy when the patient is determined to likely suffer from a thrombotic event.

In some embodiments, the patient is determined to likely to suffer from a thrombotic event if the anti-fXa activity is lower than 30 to 50 ng/ml when the fXa inhibitor is apixaban, rivaroxaban, betrixaban or edoxaban, or is lower than 0.25 to 0.5 IU/ml when the fXa inhibitor is enoxaparin.

Yet another embodiment provides a method for monitoring the recovery of a patient having suffered from intracranial hemorrhage while undergoing an anticoagulation treatment with a factor Xa (fXa) inhibitor, comprising: administering to the patient a fXa derivative that has a deletion of at least 50% of amino acid residues 6-39 of the light chain and a modification at the active site on the heavy chain, wherein the fXa derivative has reduced catalytic activity as compared to the wild-type fXa protein, and is capable of binding to the factor Xa inhibitor; obtaining a blood sample from the patient following the administration; measuring an anti-fXa activity in the sample; and determining a duration for monitoring the patient based on the risk.

In some embodiments, the method further comprises discharging the patient from monitoring when the anti-fXa activity is from 30 to 50 ng/ml when the fXa inhibitor is apixaban, rivaroxaban, betrixaban or edoxaban, or is from 0.25 to 0.5 IU/ml when the fXa inhibitor is enoxaparin.

The fXa derivative disclosed herein may be a two-chain protein comprising a light chain comprising the amino acid sequence of SEQ ID NO:3 or a first peptide having at least 85% sequence identity to SEQ ID NO:3, and a heavy chain comprising the amino acid sequence of SEQ ID NO:4 or a second peptide having at least 85% sequence identity to SEQ ID NO:4. In some embodiment, the fXa derivative is andexanet alfa.

BRIEF DESCRIPTION OF THE DRAWINGS

Provided as embodiments of this disclosure are drawings which illustrate by exemplification only, and not limitation, wherein.

DETAILED DESCRIPTION

I. Definitions

Figure 1A:
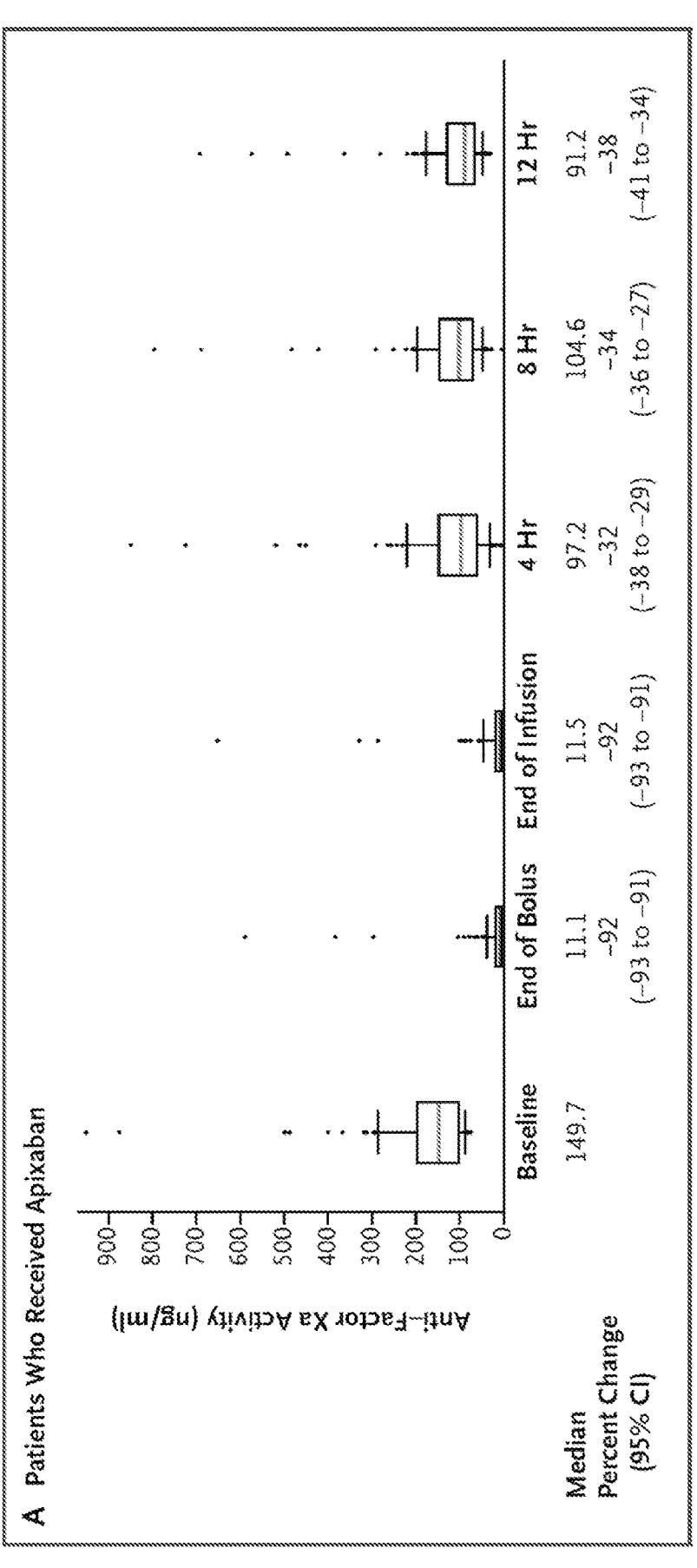
FIG. 1A-1C show the anti-factor Xa activities in patients, who had major bleeding while undergoing anticoagulant therapy, treated with the factor Xa inhibitors Apixaban (A), Rivaroxaban (B), and Enoxaparin (C).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

A "composition" is intended to mean a combination of active agent and another compound or composition, inert (for example, a detectable agent or label) or active.

"Factor Xa" or "fXa" or "fXa protein" is a serine protease in the blood coagulation pathway, which is produced from the inactive factor X (fX). The nucleotide sequence coding human factor X ("fX") can be found in GenBank with accession number "NM_000504." Upon catalytic cleavage of the first 52 residues of the heavy chain, fX is activated to fXa (SEQ ID NO. 1, Table 1). FXa contains a light chain and a heavy chain (as shown in Table 1). The first 45 amino acid residues (residues 1-45 of SEQ ID NO. 1) of the light chain is called the Gla domain because it contains 11 post-translationally modified γ-carboxyglutamic acid residues (Gla). It also contains a short (6 amino acid residues) aromatic stack sequence (residues 40-45 of SEQ ID NO. 1). Chymotrypsin digestion selectively removes the 1-44 residues resulting in Gla-domainless fXa. The serine protease catalytic domain of fXa is located on the C-terminal heavy chain. The heavy chain of fXa is highly homologous to other serine proteases such as thrombin, trypsin, and activated protein C.

"Native fXa" or "wild-type fXa" refers to the fXa naturally present in plasma or being isolated in its original, unmodified form, which possesses the biological activity of activating prothrombin therefore promoting formation of blood clot. The term includes naturally occurring polypeptides isolated from tissue samples as well as recombinantly produced fXa. "Active fXa" refers to fXa having the biological activity of activating prothrombin. "Active fXa" may be a native fXa or modified fXa that retains procoagulant activity.

As used herein, "fXa derivatives" refer to modified fXa proteins that have a modification or substantial deletion (e.g., deletion of at least 50%, 60%, 70%, 80%, or 90% of the amino acid residues 6-39 of the light chain) of the Gla-domain and a modification to the active site such that the fXa derivatives, as compared to the wild-type protein, have reduced ability in assembling into the prothrombinase complex and reduced or no catalytic activities. Still, similar to the wild-type protein, the fXa derivatives can bind and/or substantially neutralize fXa inhibitors. Examples of fXa derivatives are provided in WO2009/042962 and WO2010/117729, and biological equivalents thereof.

The term "active site" refers to the part of an enzyme or antibody where a chemical reaction occurs. A "modified active site" is an active site that has been modified structurally to provide the active site with increased or decreased chemical reactivity or specificity. Examples of active sites include, but are not limited to, the catalytic domain of human factor X comprising the 235-488 amino acid residues, and the catalytic domain of human factor Xa comprising the 195-448 amino acid residues. Examples of modified active site include, but are not limited to, the catalytic domain of human factor Xa comprising 195-448 amino acid residues in SEQ ID NOS. 2 with at least one amino acid substitution at position Arg306, Glu310, Arg347, Lys351, Lys414, or Arg424.

An example of a fXa derivative is a "Gla-domainless fXa" or "des-Gla fXa" that refers to fXa or a fXa derivative that does not have a Gla-domain and encompasses fXa derivatives bearing other modification(s) in addition to the removal of the Gla-domain. Examples of Gla-domainless fXa in this invention include, but are not limited to, fXa derivative lacking all or part of the 1-39 (or 6-39) amino acid residues of SEQ ID NO. 1.

Another example of a fXa derivative is a "Gla-deficient fXa" that refers to fXa or a fXa derivative with reduced number of free side chain γ-carboxyl groups in its Gla-domain. Like Gla-domainless fXa, Gla-deficient fXa can also bear other modifications. Gla-deficient fXa includes uncarboxylated, undercarboxylated and decarboxylated fXa. "Uncarboxylated fXa" or "decarboxylated fXa" refers to fXa derivatives that do not have the γ-carboxy groups of the γ-carboxyglutamic acid residues of the Gla domain, such as fXa having all of its Gla domain γ-carboxyglutamic acid replaced by different amino acids, or fXa having all of its side chain γ-carboxyl removed or masked by means such as amination, esterification, etc. For recombinantly expressed protein, uncarboxylated fXa is, sometimes, also called non-carboxylated fXa. "Undercarboxylated fXa" refers to fXa derivatives having reduced number of γ-carboxy groups in the Gla domain as compared with wild-type fXa, such as fXa having one or more but not all of its Gla domain γ-carboxy-glutamic acids replaced by one or more different amino acids, or fXa having at least one but not all of its side chain γ-carboxyl removed or masked by means such as amination and esterification, etc.

In some embodiments, the fXa derivatives have a deletion of at least amino acid residues 6-39 of the light chain of the wild-type fXa (see light chain in SEQ ID NO:1). In some embodiments, the fXa derivatives also have a deletion of the EGF1 domain (amino acids 46-84) and/or the EGF2 domain (amino acids 85-128 of the light chain). In some embodiments, the light chain of the fXa derivative includes at least amino acids 129-139 of the wild-type light chain (or 95-105 of SEQ ID NO:3).

SEQ ID NO: 2 (Table 2), which is also referred to as "andexanet alfa" or simply "andexanet", contains two mutations relative to the wild-type fXa". The first mutation is the deletion of amino acid residues 6-39 in the Gla-domain of fX. The second mutation is mutation of active site residue S379 to an Ala residue. This amino acid substitution corresponds to amino acid 296 of SEQ ID NOS: 1, respectively. Andexanet includes two chains, referred to as SEQ ID NO:3 (light chain) and 4 (heavy chain), respectively.

fXa derivatives also encompass those that contain mutations, post-translational modifications, and/or changes to the protein during the manufacturing process. For instance, in another aspect, the fXa derivatives, with or without the Ser379 modification, may contain modifications on the His (to Ala) and/or Asp (to Ala/Asn) residues in the catalytic triad, and a deleted or modified Gla domain. These modifications provide fXa derivatives with reduced enzymatic activity but not competing with fXa in assembling into the prothrombinase complex.

In some embodiments, the fXa derivative has a heavy chain that has one or two O-linked glycosylation. In some embodiments, the heavy chain may have a C-terminal truncation of an amino acid residue, or up to 13, 14 or 15 amino acid residues. In some embodiments, the light chain may have an N-terminal truncation.

The present disclosure provides a variety of biological equivalents of the disclosed sequences of the fXa derivatives, or alternatively polypeptides having certain sequence identity to these fXa derivatives. In one aspect, such biological equivalents retain the structural characteristics of these fXa derivatives, that is, a modified active site or heavy chain and a deleted or modified Gla domain. In another aspect, such biological equivalents retain the functional features of these fXa derivatives, that is, not competing with fXa in assembling into the prothrombinase complex and having reduced catalytic activities. In another aspect, such biological equivalents can bind and/or substantially neutralize fXa inhibitors.

TABLE 1

Polypeptide sequence of activated human factor X, fXa
(SEQ ID NO: 1)

Light Chain

| | | | | |
|---|---|---|---|---|
| 1 ANSFLEEMKK | GHLERECMEE | TCSYEEAREV | FEDSDKTNEF | WNKYKDGDQC | ETSPCQNQGK |
| 61 CKDGLGEYTC | TCLEGFEGKN | CELFTRKLCS | LDNGDCDQFC | HEEQNSVVCS | CARGYTLADN |
| 121 GKACIPTGPY | PCGKQTLER | | | | |

Heavy Chain

| | | | | | |
|---|---|---|---|---|---|
| 181 | | IVGGQE | CKDGECPWQA | LLINEENEGF | CGGTILSEFY | ILTAAHCLYQ |
| 241 AKRFKVRVGD | RNTEQEEGGE | AVHEVEVVIK | HNRFTKETYD | FDIAVLRLKT | PITFRMNVAP |
| 301 ACLPERDWAE | STLMTQKTGI | VSGFGRTHEK | GRQSTRLKML | EVPYVDRNSC | KLSSSFIITQ |
| 361 NMFCAGYDTK | QEDACQGDAG | GPHVTRFKDT | YFVTGIVSWG | EGCARKGKYG | IYTKVTAFLK |
| 421 WIDRSMKTRG | LPKAKSHAPE | VITSSPLK | | | |

TABLE 2

| Polypeptide sequence of andexanet (SEQ ID NO: 2) | | | | |
|---|---|---|---|---|
| Light Chain (SEQ ID NO: 3) | | | | |
| 1 ANSFL | | F | WNKYKDGDQC | ETSPCQNQGK |
| 61 CKDGLGEYTC | TCLEGFEGKN | CELFTRKLCS | LDNGDCDQFC | HEEQNSVVCS CARGYTLADN |
| 121 GKACIPTGPY | PCGKQTLER | | | |
| Heavy Chain (SEQ ID NO: 4) | | | | |
| 181 | IVGGQE | CKDGECPWQA | LLINEENEGF | CGGTILSEFY ILTAAHCLYQ |
| 241 AKRFKVRVGD | RNTEQEEGGE | AVHEVEVVIK | HNRFTKETYD | FDIAVLRLKT PITFRMNVAP |
| 301 ACLPERDWAE | STLMTQKTGI | VSGFGRTHEK | GRQSTRLKML | EVPYVDRNSC KLSSSFIITQ |
| 361 NMFCAGYDTK | QEDACQGDAG | GPHVTRFKDT | YFVTGIVSWG | EGCARKGKYG IYTKVTAFLK |
| 421 WIDRSMKTRG | LPKAKSHAPE | VITSSPLK | | |

The term "factor Xa inhibitors" or "inhibitors of factor Xa" refer to compounds that can inhibit, either directly or indirectly, the coagulation factor Xa's activity of catalyzing conversion of prothrombin to thrombin in vitro and/or in vivo.

"Direct factor Xa inhibitors" or "direct fXa inhibitors" bind to the fXa directly and non-limiting examples include apixaban, rivaroxaban, edoxaban, betrixaban, NAP-5, rNAPc2, tissue factor pathway inhibitor, DX-DX-9065a (as described in, e.g., Herbert, J. M., et al, *J Pharmacol Exp Ther.* 1996 276(3):1030-8), YM-60828 (as described in, e.g., Taniuchi, Y., et al, *Thromb Haemost.* 1998 79(3):543-8), YM-150 (as described in, e.g., Eriksson, B. I. et. al, *Blood* 2005; 106(11), Abstract 1865), TAK-442, PD-348292 (as described in, e.g., Pipeline Insight: Antithrombotics— Reaching the Untreated Prophylaxis Market, 2007), ota-mixaban, LY517717 (as described in, e.g., Agnelli, G., et al, *J. Thromb. Haemost.* 2007 5(4):746-53), GSK913893, razaxaban, or a pharmaceutically acceptable salt thereof, and combinations thereof.

"Indirect factor Xa inhibitors" or "indirect fXa inhibitors" inhibit the fXa activity via one or more other factors. Non-limiting examples of indirect factor Xa inhibitors include enoxaparin, fondaparinux, idraparinux, biotinylated idraparinux, fragmin, tinzaparin, low molecular weight heparin ("LMWH"), and combinations thereof.

In one embodiment, the factor Xa inhibitor is selected from apixaban, rivaroxaban, edoxaban, betrixaban, enoxaparin and combinations thereof.

II. Assessment of Hemostatic Efficacy

Anticoagulants serve a need in the marketplace in treatment or prevention of undesired thrombosis in patients with a tendency to form blood clots, such as, for example, those patients having clotting disorders, confined to periods of immobility or undergoing medical surgeries. One of the major limitations of anticoagulant therapy, however, is the bleeding risk associated with the treatments, and limitations on the ability to rapidly reverse the anticoagulant activity in case of overdosing or if an urgent surgical procedure is required.

Andexanet alfa (andexanet) is a recombinant modified human factor Xa decoy protein that can reverse the inhibition of factor Xa, and thus is an effective antidote to factor Xa-based anticoagulant treatments.

In certain situations, in particular in elderly patients, monitoring of the efficacy of andexanet is important, such as when additional andexanet is needed, or when there is an anticoagulant overdosing concern. Monitoring of hemostatic efficacy, however, can be difficult. For instance, measurement of hemostatic efficacy may require serial CT or MRI scans of hematoma volume and/or thickness change over 12 hours or more.

Contrary to the observation that there was no correlation between anti-factor Xa activity and hemostatic efficacy in the overall population, a good correlation was surprisingly detected in intracranial hemorrhage patients.

In accordance with one embodiment of the present disclosure, therefore, provided is a method for assessing the hemostatic efficacy in a patient having suffered from intracranial hemorrhage while undergoing an anticoagulation treatment with a factor Xa (fXa) inhibitor. In some embodiments, the method entails administering to the patient a fXa derivative of the present disclosure, obtaining a blood sample from the patient following the administration and measuring an anti-fXa activity in the sample. The anti-fXa activity can be used to predict the hemostatic efficacy in the patient.

"Intracranial hemorrhage," or ICH, refers to bleeding within the skull or brain. Intracranial hemorrhage is a serious medical emergency because the buildup of blood within the skull can lead to increases in intracranial pressure, which can crush delicate brain tissue or limit its blood supply. Severe increases in intracranial pressure (ICP) can cause brain herniation, in which parts of the brain are squeezed past structures in the skull. Intracranial bleeding occurs when a blood vessel within the skull is ruptured or leaks. It can result from physical trauma or nontraumatic causes. Anticoagulant therapy, as well as disorders with blood clotting can heighten the risk that an intracranial hemorrhage will occur.

In some embodiments, the patient has suffered from intracranial hemorrhage. In some embodiments, the patient has suffered from a subtype of intracranial hemorrhage, such as intra-axial bleed or hemorrhage (cerebral hemorrhage), extra-axial bleed (including epidural hemorrhage, subdural hemorrhage, and subarachnoid hemorrhage), epidural hematoma, subdural hematoma, or subarachnoid hemorrhage.

"Intra-axial hemorrhage" is bleeding within the brain itself, or cerebral hemorrhage. This subtype includes intra-parenchymal hemorrhage, or bleeding within the brain tissue, and intraventricular hemorrhage, bleeding within the brain's ventricles (particularly of premature infants). Intra-axial hemorrhages are more dangerous and harder to treat than extra-axial bleeds.

"Extra-axial hemorrhage" refers to bleeding that occurs within the skull but outside of the brain tissue. Examples of extra-axial hemorrhage include epidural hemorrhage, sub-dural hemorrhage, and subarachnoid hemorrhage.

"Epidural hemorrhage" (extradural hemorrhage) which occurs between the dura mater (the outermost meninx) and the skull, is caused by trauma. It may result from laceration of an artery, most commonly the middle meningeal artery. This is a dangerous type of injury because the bleed is from a high-pressure system and deadly increases in intracranial pressure can result rapidly. However, it is the least common type of meningeal bleeding and is seen in 1% to 3% cases of head injury.

"Subdural hemorrhage" results from tearing of the bridg-ing veins in the subdural space between the dura and arachnoid mater.

"Subarachnoid hemorrhage," which occurs between the arachnoid and pia meningeal layers, like intraparenchymal hemorrhage, can result either from trauma or from ruptures of aneurysms or arteriovenous malformations. Blood is seen layering into the brain along sulci and fissures, or filling subarachnoid cisterns (most often the chiasmatic cistern because of the presence of the anterior cerebral arteries of the circle of Willis and their branchpoints within that space). The classic presentation of subarachnoid hemorrhage is the sudden onset of a severe headache (a thunderclap headache). This can be a dangerous entity, and requires emergent neurosurgical evaluation, and sometimes urgent interven-tion.

"Epidural hematoma" (EDH) is a rapidly accumulating hematoma between the dura mater and the cranium. These patients have a history of head trauma with loss of con-sciousness, then a lucid period, followed by loss of con-sciousness. Clinical onset occurs over minutes to hours. Many of these injuries are associated with lacerations of the middle meningeal artery. A "lenticular," or convex, lens-shaped extracerebral hemorrhage that does not cross suture lines will likely be visible on a CT scan of the head.

"Subdural hematoma" occurs when there is tearing of the bridging vein between the cerebral cortex and a draining venous sinus. At times they may be caused by arterial lacerations on the brain surface. Acute subdural hematomas are usually associated with cerebral cortex injury as well and hence the prognosis is not as good as extra dural hematomas. Clinical features depend on the site of injury and severity of injury. Patients may have a history of loss of consciousness but they recover and do not relapse. Clinical onset occurs over hours. A crescent shaped hemorrhage compressing the brain that does cross suture lines will be noted on CT of the head. Craniotomy and surgical evacuation is required if there is significant pressure effect on the brain. Complica-tions include focal neurologic deficits depending on the site of hematoma and brain injury, increased intracranial pres-sure leading to herniation of brain and ischemia due to reduced blood supply and seizures.

A "subarachnoid hemorrhage" is bleeding into the suba-rachnoid space—the area between the arachnoid membrane and the pia mater surrounding the brain. Besides from head injury, it may occur spontaneously, usually from a ruptured cerebral aneurysm. Symptoms of SAH include a severe headache with a rapid onset (thunderclap headache), vom-iting, confusion or a lowered level of consciousness, and sometimes seizures. The diagnosis is generally confirmed with a CT scan of the head, or occasionally by lumbar puncture. Treatment is by prompt neurosurgery or radiologi-cally guided interventions with medications and other treat-ments to help prevent recurrence of the bleeding and com-plications.

The fXa derivative may be administered via either intra-venous administration by bolus or a combination of bolus and infusion or by subcutaneous administration. In certain embodiments, about 10 to about 20% of the formulation is administered as a bolus and the remaining formulation is infused over a period until bleeding has substantially ceased. It is contemplated that the infusion can be administered for about 6 hours, or about 6 to about 12 hours, or about 12 to about 24 hours or 48 hours.

In some embodiments, the fXa derivative is administered as an intravenous (IV) bolus, with a target rate of about 30 mg/min, followed by continuous infusion for up to 120 minutes. In some embodiments, the initial IV bolus includes about 400 mg of the fXa derivative. In some embodiments, the initial IV bolus includes about 800 mg of the fXa derivative. In some embodiments, the follow-on IV infusion administers about 4 mg/min for 120 minutes. In some embodiments, the follow-on IV infusion administers about 8 mg/min for 120 minutes.

In one aspect, the fXa derivative is administered at least about 5 minutes after the bleeding (blood loss) initiated. Alternatively, the fXa derivative is administered at least about 10 minutes, 15 minutes, 20 minutes, 25 minutes or 30 minutes after the bleeding has initiated.

Anti-fXa activities can be measured with methods known in the art, such as the chromogenic assay disclosed in Example 4 of WO2009/042962 and Siegal et al., *N Engl J Med* 2015; 373:2413-24. For instance, to measure the anti-fXa activity, purified active fXa, different concentrations of the fXa inhibitor (e.g., apixaban, rivaroxaban, edoxaban, betrixaban, and enoxaparin) and andexanet are added to 20 mM Tris, 150 mM NaCl, 5 mM $Ca^{2+}$, and 0.1% Bovine Serum Albumin (BSA). After incubation at room tempera-ture for 20 minutes, 100 µM Spectrozyme-fXa (a factor Xa chromogenic substrate, Chromogenix) is added to the mix-ture and the rate of substrate cleavage is monitored continu-ously for 5 minutes at 405 nanometer (nm) by a plate reader.

The measured anti-fXa activity can be used to compute/estimate the hemostatic efficacy based on their correlation as demonstrated in the present disclosure. In some embodi-ments, the estimation takes the anti-fXa activities both before the administration of the fXa derivative and the after the administration as input data points.

The measurement after the treatment can be made at different time points. For instance, the blood sample can be obtained within 20-35 minutes after the beginning of a treatment and within 10 minutes after the end of the treat-ment. Blood samples can also be obtained up to 1, 2, 3, 4, 6, 12, 18, 24, 36, 48 hours or more after the treatment, in some embodiments.

III. Medical Intervention Based on Assessment

The measured anti-fXa activity can also be directly used to help direct medical intervention, without estimating the hemostatic efficacy first. For instance, based on the anti-fXa activity, a healthcare provider may determine (a) whether to administer to the patient a second dose of the fXa derivative, (b) a likelihood that the patient will suffer from a thrombotic event, (c) a minimum time for monitoring or treatment, and/or (d) whether the patient can undergo a surgical pro-cedure.

In one embodiment, a method is provided for treating intracranial hemorrhage in a patient undergoing an anticoagulation treatment with a factor Xa (fXa) inhibitor. The method can include administering to the patient a fXa derivative of the present disclosure, obtaining a blood sample from the patient following the administration; measuring an anti-fXa activity in the sample; and administering to the patient a second dose of the fXa derivative if the anti-fXa activity is above a predetermined anti-fXa activity threshold.

The "predetermined anti-fXa activity threshold" can be determined for any particular patient population and/or the involved medical intervention. In some embodiments, the predetermined anti-fXa activity threshold may be a value between 30 and 50 ng/ml for a direct fXa inhibitor (e.g., apixaban, rivaroxaban, edoxaban, or betrixaban), or between 0.25 and 0.5 international unit (IU)/ml when the fXa inhibitor is an indirect inhibitor (e.g., enoxaparin). Anti-fXa activities in these ranges, in some embodiments, can be considered to indicate suitable treatment results.

Accordingly, if the measured anti-fXa activity is higher than 30, 40, 50, 60, 70, 80, 90, or 100 ng/ml for a direct fXa inhibitor, another dosing of the fXa derivative may be warranted and is administered. Likewise, if the measured anti-fXa activity is higher than 0.15, 0.2, 0.25, 0.3, 0.4, 0.5, 0.6, 0.7, 0.8, 0.9, or 1 IU/ml for an indirect fXa inhibitor, another dosing of the fXa derivative may be warranted and is administered.

In another embodiment, a method is provided for conducting a surgery in a patient having suffered from intracranial hemorrhage while undergoing an anticoagulation treatment with a factor Xa (fXa) inhibitor. In some embodiments, the method entails administering to the patient a fXa derivative of the present disclosure, obtaining a blood sample from the patient following the administration; measuring an anti-fXa activity in the sample; and conducting the surgery in the patient if the anti-fXa activity is below a predetermined anti-fXa activity threshold.

Here, the "predetermined anti-fXa activity threshold" can also be determined empirically. Nevertheless, in some embodiments, in some embodiments, the predetermined anti-fXa activity threshold may be a value between 30 and 50 ng/ml for a direct fXa inhibitor (e.g., apixaban, rivaroxaban, betrixaban, or edoxaban), or between 0.25 and 0.5 IU/ml when the fXa inhibitor is an indirect inhibitor (e.g., enoxaparin). Anti-fXa activities in these ranges, in some embodiments, can be considered to indicate suitable treatment results with the fXa derivative.

Accordingly, in some embodiments, if the measured anti-fXa activity is lower than 50, 40, 30, 25, 20, 15, 10, or 5 ng/ml for a direct fXa inhibitor, the patient may be suitable for a surgery. If the measured anti-fXa activity is too high, then the patient may be at high risk for hemorrhage during the indicated surgery. Likewise, if the measured anti-fXa activity is lower than 1, 0.9, 0.8, 0.7, 0.6, 0.5, 0.4, 0.3, 0.25, 0.2, or 0.15 IU/ml for an indirect fXa inhibitor, the patient may be suitable for a surgery.

Also provided, in another embodiment, is a method for preventing a thrombotic event in a patient having suffered from intracranial hemorrhage while undergoing an anticoagulation treatment with a factor Xa (fXa) inhibitor. In some embodiments, the method entails administering to the patient a fXa derivative of the present disclosure, obtaining a blood sample from the patient following the administration; measuring an anti-fXa activity in the sample; determining a likelihood that the patient will suffer from a thrombotic event based on the anti-fXa activity; and administering to the patient an anticoagulation therapy when the patient is determined to likely suffer from a thrombotic event.

In some embodiments, the predetermined anti-fXa activity threshold may be a value between 30 and 50 ng/ml for a direct fXa inhibitor (e.g., apixaban, rivaroxaban, betrixaban, or edoxaban), or between 0.25 and 0.5 IU/ml when the fXa inhibitor is an indirect inhibitor (e.g., enoxaparin). Anti-fXa activities in these ranges, in some embodiments, can be considered to indicate that the patient is relatively safe from a thrombotic event. If the anti-fXa activity is too low, then the patient may have risk of developing a thrombotic event, and thus suitable preventive measures are recommended.

Accordingly, in some embodiments, if the measured anti-fXa activity is lower than 50, 40, 30, 25, 20, 15, 10, or 5 ng/ml for a direct fXa inhibitor, a suitable prescription is recommended to the patient to prevent a likely thrombotic event. Likewise, if the measured anti-fXa activity is lower than 1, 0.9, 0.8, 0.7, 0.6, 0.5, 0.4, 0.3, 0.25, 0.2, or 0.15 IU/ml for an indirect fXa inhibitor, the patient may receive a medication to prevent thrombotic event. In some embodiments, the medication is an anti-coagulant treatment, such as with a factor Xa inhibitor.

In some embodiments, the present disclosure provides a method for monitoring the recovery of a patient having suffered from intracranial hemorrhage while undergoing an anticoagulation treatment with a factor Xa (fXa) inhibitor. In some embodiments, the method entails administering to the patient a fXa derivative of the present disclosure, obtaining a blood sample from the patient following the administration, measuring an anti-fXa activity in the sample, and determining a duration for monitoring the patient based on the risk.

In the intracranial hemorrhage population, there is a risk of hematoma expansion in 1/3 of patients and a risk of thrombotic event in 5-15% of patients. The risk decreases significantly after 2-3 days, and so that is when patients are typically discharged. Following a treatment with a fXa derivative, if the anti-fXa activity level is within a safe window, e.g., 30 to 50 ng/ml for a direct fXa inhibitor or from 0.25 to 0.5 IU/ml for an indirect fXa inhibitor, less than 24 hours, less than 36 hours, or less than 48 hours after treatment, the patient can be discharged. If the measured anti-fXa activity level is much higher or lower than this, further monitoring may be required. As disclosed above, if the anti-fXa activity is too high, perhaps another dose of the fXa derivative can be given. If the anti-fXa activity is too low, perhaps more fXa inhibitors can be given to prevent thrombotic events.

IV. Factor Xa Derivative Compositions

In various embodiments, a factor Xa derivative is administered to a patient. Accordingly, compositions including the factor Xa derivative are also provided. In some embodiments, the compositions further include a pharmaceutically acceptable carrier. In some embodiments, the fXa derivative is conjugated with a moiety capable of extending the circulating half-life of the derivative.

"Pharmaceutically acceptable carriers" refers to any diluents, excipients, or carriers that may be used in the compositions of the disclosure. Pharmaceutically acceptable carriers include saline, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in *Remington's Pharmaceutical Sciences*, Mack Publishing Company, a standard reference text in this field. They are preferably selected with respect to the intended form of administration, that is, oral tablets, capsules, elixirs, syrups and the like, and consistent with conventional pharmaceutical practices.

The formulations of the disclosure can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, injections, emulsions, elixirs, suspensions or solutions. Formulations may optionally contain stabilizers, pH modifiers, surfactants, bioavailability modifiers and combinations of these.

In one embodiment, the fXa derivative is lyophilized. Methods for lyophilizing polypeptides are well known in the art. In some embodiments, the fXa derivative is provided in single-use vials, containing 100, 200 or 400 mg of the lyophilized fXa derivative formulated with the inactive ingredients tromethamine (Tris), L-arginine hydrochloride, sucrose (2% w/v), mannitol (5% w/v), and polysorbate 80 (0.01% w/v) at pH 7.8. It can be reconstituted with sterile water for injection for intravenous (IV) administration.

Pharmaceutical formulations may also be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The formulations are for administration to a mammal, preferably a human being. Such formulations of the disclosure may be administered in a variety of ways, preferably parenterally.

The term "parenteral" as used herein includes subcutaneous, intravenous, intramuscular, intra-articular, intra-synovial, intrasternal, intrathecal, intrahepatic, intralesional and intracranial injection or infusion techniques. However, in cases where the fXa inhibitor being neutralized has a long plasma half-life, a continuous infusion or a sustained release formulation may be required to bind to the fXa inhibitor and such free up the active fXa prior to the clearance of the fXa inhibitor from the body. Therefore, in one aspect, the formulation is administered to the subject as a bolus. In another aspect, the formulation is administered by infusion. In another aspect, the formulation is administered by a combination of bolus and infusion.

Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compositions may be formulated for parenteral administration by injection such as by bolus injection or continuous infusion. A unit dosage form for injection may be in ampoules or in multi-dose containers.

In addition to dosage forms described above, pharmaceutically acceptable excipients and carriers and dosage forms are generally known to those skilled in the art and are included in the disclosure. It should be understood that a specific dosage and treatment regimen for any particular patient will depend upon a variety of factors, including the activity of the specific fXa derivative employed, the age, body weight, general health, sex and diet, renal and hepatic function of the patient, and the time of administration, rate of excretion, drug combination, judgment of the treating physician or veterinarian and severity of the particular disease being treated.

EXAMPLES

The disclosure is further understood by reference to the following examples, which are intended to be purely exemplary of the disclosure. The present disclosure is not limited in scope by the exemplified embodiments, which are intended as illustrations of single aspects of the disclosure only. Any methods that are functionally equivalent are within the scope of the disclosure. Various modifications of the disclosure in addition to those described herein will become apparent to those skilled in the art from the foregoing description and accompanying figures. Such modifications fall within the scope of the appended claims.

Example 1

Treatment of Factor Xa Inhibitor-Associated Bleeding with Andexanet Alfa

This example tested the ability of andexanet alfa to reduce anti-factor Xa activity and to restore hemostatic efficacy in patients who suffered from acute major bleeding associated with factor Xa inhibitor-based anticoagulant treatments.

This study evaluated 352 patients who had acute major bleeding within 18 hours after administration of a factor Xa inhibitor. The patients received a bolus of andexanet, followed by a 2-hour infusion. The coprimary outcomes were the percent change in anti-factor Xa activity after andexanet treatment and the percentage of patients with excellent or good hemostatic efficacy at 12 hours after the end of the infusion, with hemostatic efficacy adjudicated on the basis of prespecified criteria. Efficacy was assessed in the subgroup of patients with confirmed major bleeding and baseline anti-factor Xa activity of at least 75 ng per milliliter (or $\geq 0.25$ IU per milliliter for those receiving enoxaparin).

Patients had a mean age of 77 years, and most had substantial cardiovascular disease. Bleeding was predominantly intracranial (in 227 patients [64%]) or gastrointestinal (in 90 patients [26%]). In patients who had received apixaban, the median anti-factor Xa activity decreased from 149.7 ng per milliliter at baseline to 11.1 ng per milliliter after the andexanet bolus (92% reduction; 95% confidence interval [CI], 91 to 93); in patients who had received rivaroxaban, the median value decreased from 211.8 ng per milliliter to 14.2 ng per milliliter (92% reduction; 95% CI, 88 to 94). Excellent or good hemostasis occurred in 204 of 249 patients (82%) who could be evaluated. Within 30 days, death occurred in 49 patients (14%) and a thrombotic event in 34 (10%). Reduction in anti-factor Xa activity was not predictive of hemostatic efficacy overall but was modestly predictive in patients with intracranial hemorrhage.

In patients with acute major bleeding associated with the use of a factor Xa inhibitor, treatment with andexanet markedly reduced anti-factor Xa activity, and 82% of patients had excellent or good hemostatic efficacy at 12 hours, as adjudicated according to prespecified criteria.

Methods:

Study Design and Oversight

This was a multicenter, prospective, open-label, single-group study. The protocol, consent forms, and ancillary materials were approved by institutional review boards at each center.

Study Population

Patients were enrolled at 63 centers in North America and Europe. Patients were eligible if they were at least 18 years of age, presented with acute major bleeding, and had received within 18 hours one of the following: apixaban, rivaroxaban, or edoxaban at any dose or enoxaparin at a dose of at least 1 mg per kilogram of body weight per day. Acute major bleeding was defined as one or more of the following features: potentially life-threatening bleeding with signs or symptoms of hemodynamic compromise (e.g., severe hypotension, poor skin perfusion, mental confusion, or low cardiac output that could not otherwise be explained); bleeding associated with a decrease in the hemoglobin level of at least 2 g per deciliter (or a hemoglobin level of $\leq 8$ g per deciliter if no baseline hemoglobin level was available); or bleeding in a critical area or organ (e.g., retroperitoneal, intraarticular, pericardial, epidural, or intracranial bleeding or intramuscular bleeding with compartment syndrome). Written informed consent was obtained from all the patients, whether directly from the patient, by proxy consent from a legally authorized representative, or by emergency consent.

Key exclusion criteria were planned surgery within 12 hours after andexanet treatment (with the exception of minimally invasive surgery or procedure); intracranial hemorrhage in a patient with a score of less than 7 on the Glasgow Coma Scale (scores range from 15 [normal] to 3 [deep coma]) or an estimated hematoma volume of more than 60 cc; expected survival of less than 1 month; the occurrence of a thrombotic event within 2 weeks before enrollment; or use of any of the following agents within the previous 7 days: vitamin K antagonist, dabigatran, prothrombin complex concentrate, recombinant factor VIIa, whole blood, or plasma.

Study Procedures and Data Collection

Eligible, consenting patients received an andexanet bolus over a period of 15 to 30 minutes, followed by a 2-hour infusion of the drug. The following doses were used in the initial protocol: for all patients who had received apixaban and those who had received rivaroxaban more than 7 hours before bolus administration, the bolus dose was 400 mg over a period of 15 minutes and the infusion dose was 480 mg. For patients who had received enoxaparin, edoxaban, or a dose of rivaroxaban 7 hours or less before bolus administration or at an unknown time, the bolus dose was 800 mg over a period of 30 minutes and the infusion dose was 960 mg. With protocol amendment 4, there was a minor modification to this administration plan.

Blood samples were obtained to measure anti-factor Xa activity and the unbound fraction of the plasma level of factor Xa inhibitor before and during andexanet treatment and at 4, 8, and 12 hours after the end of treatment.

For patients with intracranial hemorrhage, CT or MRI of the head was expected to be performed within 2 hours before andexanet treatment and at 1 hour and 12 hours after the end of andexanet treatment.

Study Outcomes

The study had two coprimary efficacy outcomes: the percent change from baseline in anti-factor Xa activity after andexanet treatment and the percentage of patients with excellent or good hemostatic efficacy 12 hours after the andexanet infusion, with hemostatic efficacy assessed by an independent adjudication committee on the basis of prespecified criteria. The primary safety outcomes were death, thrombotic events, and the development of antibodies to andexanet or to native factor X and factor Xa. Although some patients had their final safety visit completed up to 45 days after andexanet treatment, all analyses were censored at 30 days.

Statistical Analysis

Safety analyses included all the patients who had received andexanet. The efficacy analysis population included only patients who retrospectively met both of two criteria: baseline anti-factor Xa activity of at least 75 ng per milliliter (or $\geq 0.25$ IU per milliliter for patients receiving enoxaparin) and confirmed major bleeding at presentation, as determined by the adjudication committee. Initially, a sample of 250 patients was planned, which would provide 80% power to show that the percentage of patients with excellent or good hemostatic efficacy was more than 50%. The sample was adjusted to 350 patients in protocol amendment to meet new regulatory requirements for sufficient numbers of patients for each factor Xa inhibitor and to have at least 120 patients with intracranial hemorrhage in the efficacy analysis population.

Continuous variables are summarized as mean and standard deviation or median and interquartile range; categorical variables are presented as frequencies. Percent change from baseline in anti-factor Xa activity was computed with a two-sided nonparametric confidence interval for the median. Percentages of patients with effective hemostasis are presented with a 95% confidence interval calculated with the binomial test. The association between hemostatic efficacy and a change in anti-factor Xa activity was examined with the use of receiver-operating-characteristic (ROC) curves. Analyses were performed with the use of SAS software, version 9.4 (SAS Institute).

Results:

All the 352 patients received andexanet and were followed for at least 30 days or until death. Patients had a mean age of 77 years; baseline medical history included myocardial infarction in 48 patients (14%), stroke in 69 (20%), and deep-vein thrombosis in 67 (19%) (Table 1). Atrial fibrillation was the primary indication for anticoagulation in 280 patients (80%). There were 128 patients (36%) receiving rivaroxaban (median daily dose, 20 mg), 194 (55%) receiving apixaban (median daily dose, 10 mg), 10 (3%) receiving edoxaban (daily dose, 30 mg [5 patients] or 60 mg [5 patients]), and 20 (6%) receiving enoxaparin. The primary site of bleeding was intracranial in 227 patients (64%) and gastrointestinal in 90 (26%). There were 254 patients (72%) who met the criteria for the efficacy population (adjudicated to meet the criteria for bleeding severity and with baseline anti-factor Xa activity of ≥75 ng per milliliter, or ≥0.25 IU per milliliter for those receiving enoxaparin).

Anti-Factor Xa Activity

In the efficacy population, among the 134 patients who were receiving apixaban, the median value for anti-factor Xa activity was reduced from 149.7 ng per milliliter at baseline to 11.1 ng per milliliter at the end of the bolus administration, a 92% reduction (95% confidence interval [CI], 91 to 93) (FIG. 1). Among the 100 patients who were receiving rivaroxaban, the median value for anti-factor Xa activity fell from 211.8 ng per milliliter at baseline to 14.2 ng per milliliter at the end of the bolus administration, a 92% reduction (95% CI, 88 to 94). Among the 16 patients who were receiving enoxaparin, the median value for anti-factor Xa activity decreased from 0.48 IU per milliliter at baseline to 0.15 IU per milliliter at the end of the bolus administration, a 75% reduction (95% CI, 66 to 79). At 4, 8, and 12 hours after andexanet infusion, the median value for anti-factor Xa activity was reduced from baseline by 32%, 34%, and 38%, respectively, for apixaban and by 42%, 48%, and 62%, respectively, for rivaroxaban.

Figure 1B:
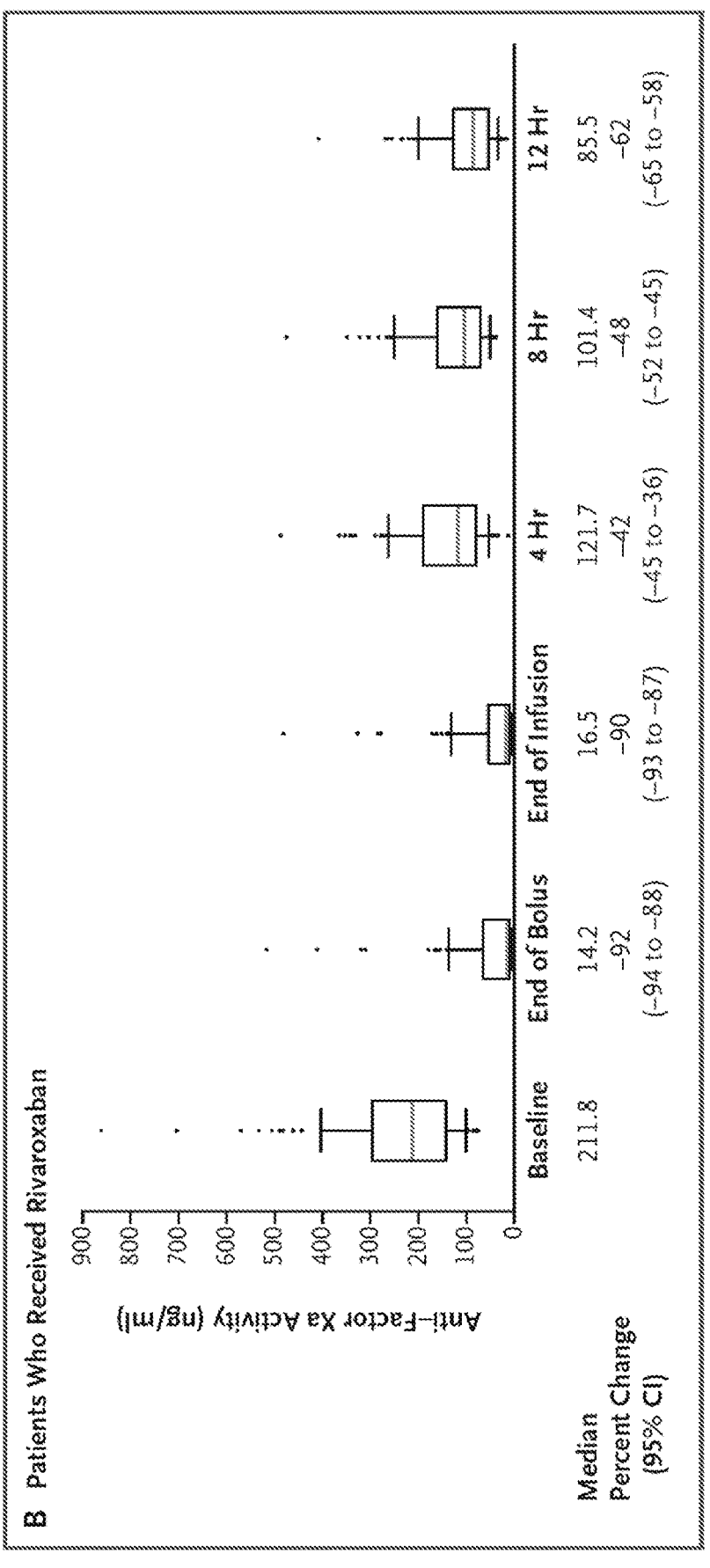
Figure 1C:
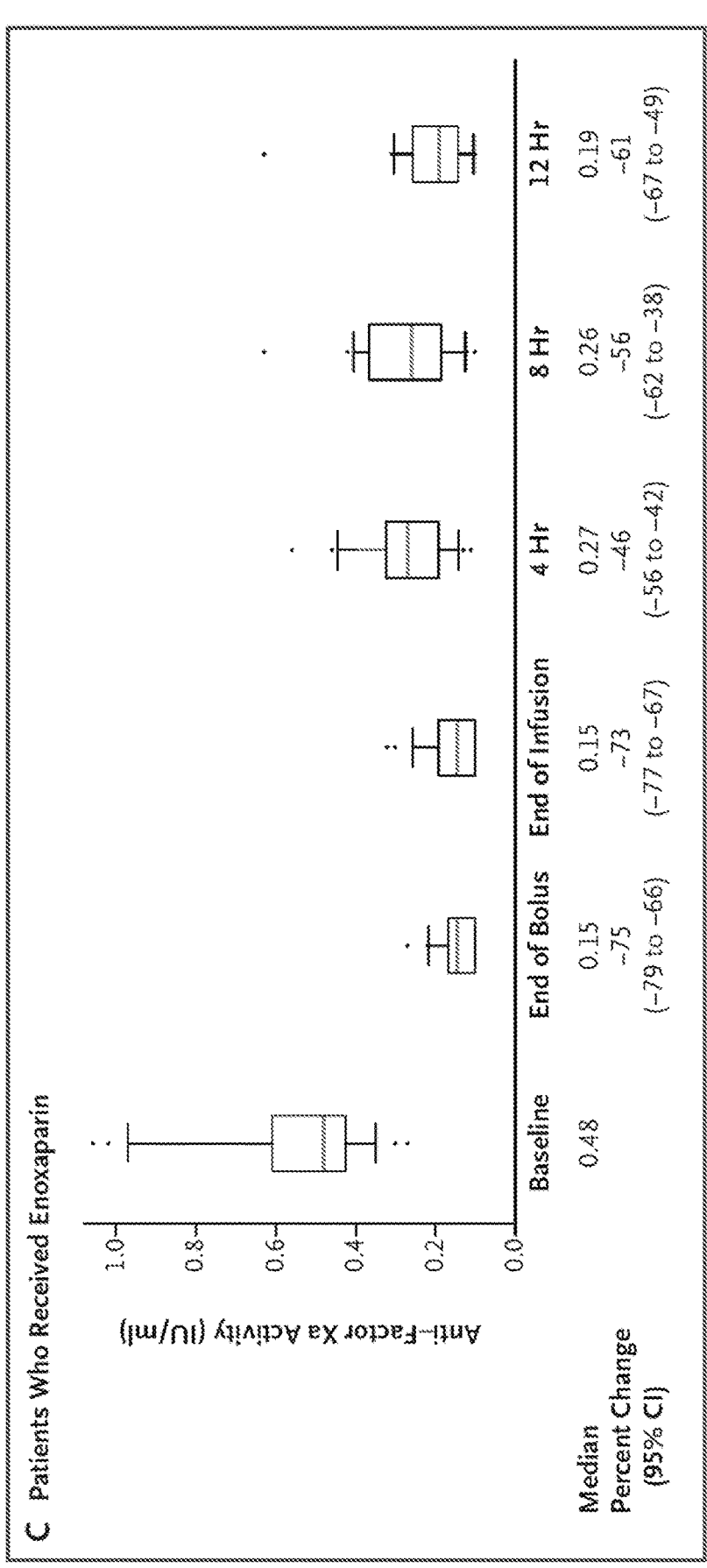

In FIG. 1A-1C, The median for each level of anti-factor Xa activity at each time point is marked as a horizontal line within the box. The top and bottom of the box denote the 75th and 25th percentiles, respectively, and the whiskers

TABLE 1

| Characteristics of the Patients at Baseline* | | |
| --- | --- | --- |
| Characteristic | Safety Population (N = 352) | Efficacy Population (N = 254) |
| Age-yr | 77.4 ± 10.8 | 77.1 ± 11.1 |
| Male sex-no. (%) | 187 (53) | 129 (51) |
| White race-no. (%)† | 307 (87) | 222 (87) |
| Body-mass index‡ | 27.0 ± 5.9 | 27.0 ± 6.2 |
| Estimated creatinine clearance-no. (%)§ | | |
| <30 ml/min | 33 (9) | 27 (11) |
| 30 to <60 ml/min | 137 (39) | 104 (41) |
| ≥60 ml/min | 167 (47) | 113 (44) |
| Missing data | 15 (4) | 10 (4) |
| Primary indication for anticoagulation-no. (%)¶ | | |
| Atrial fibrillation | 280 (80) | 201 (79) |
| Venous thromboembolism‖ | 61 (17) | 46 (18) |
| Other | 11 (3) | 7 (3) |
| Medical history-no. (%) | | |
| Myocardial infarction | 48 (14) | 36 (14) |
| Stroke | 69 (20) | 57 (22) |
| Deep-vein thrombosis | 67 (19) | 53 (21) |
| Pulmonary embolism | 41 (12) | 28 (11) |
| Atrial fibrillation | 286 (81) | 204 (80) |
| Heart failure | 71 (20) | 56 (22) |
| Diabetes mellitus | 107 (30) | 80 (31) |
| Factor Xa inhibitor-no. (%) | | |
| Rivaroxaban | 128 (36) | 100 (39) |
| Apixaban†† | 194 (55) | 134 (53) |
| Enoxaparin | 20 (6) | 16 (6) |
| Edoxaban | 10 (3) | 4 (2) |
| Site of bleeding-no. (%) | | |
| Gastrointestinal | 90 (26) | 62 (24) |
| Intracranial | 227 (64) | 171 (67) |
| Other | 35 (10) | 21 (8) |

*Plus-minus values are means ±SD. Percentages may not total 100 because of rounding.

†Race was reported by the investigators.

‡The body-mass index is the weight in kilograms divided by the square of the height in meters.

§Creatinine clearance was estimated according to the Cockcroft-Gault formula.

¶For some patients, more than one primary indication was recorded. If atrial fibrillation was present, it was considered primary. Venous thromboembolism, if recorded, was considered primary in the remaining patients.

‖Venous thromboembolism includes the treatment or prevention of deep-vein thrombosis and pulmonary embolism.

††In one patient who reported receiving apixaban, analysis of plasma indicated a high concentration of rivaroxaban.

indicate the 90th and 10th percentiles. Outliers are shown as dots. The bolus of andexanet was delivered over a period of 15 to 30 minutes, and the drug infusion lasted 2 hours. Subsequent time points are measured from the end of the infusion. The plots for the 134 patients who received apixaban, the 100 who received rivaroxaban, and the 16 who received enoxaparin are shown in FIGS. 1A, 1B, and 1C, respectively. (The 4 patients in the efficacy analysis who received edoxaban are not shown.) The numbers below the graphs show the median values, the percentage change in median values from baseline, and the 95% confidence intervals (CI) for this change.

Hemostatic Efficacy

Figure 2:
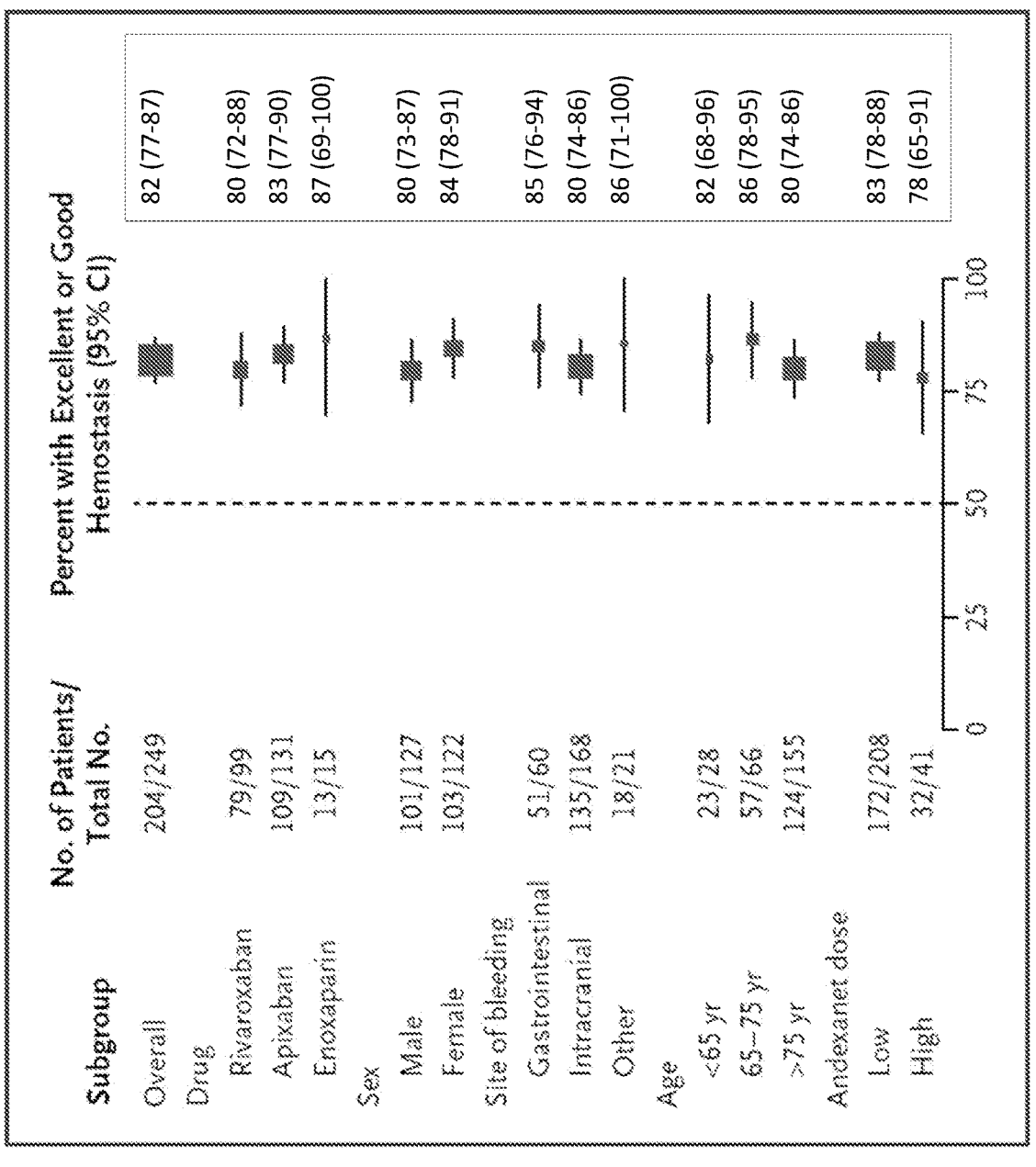
FIG. 2 shows the hemostatic efficacies measured in the samples.

Of the 254 patients in the efficacy analysis, 249 could be evaluated for hemostatic efficacy, and 204 (82%) were adjudicated as having excellent or good hemostatic efficacy at 12 hours (95% CI, 77 to 87) (FIG. 2). Of these, 171 were adjudicated as having excellent hemostatic efficacy and 33 as having good hemostatic efficacy. The percentages of patients with excellent or good efficacy were 85% (95% CI, 76 to 94) for gastrointestinal bleeding and 80% (95% CI, 74 to 86) for intracranial bleeding.

FIG. 2 shows the percentages of patients in the efficacy analysis who had excellent or good hemostatic efficacy at 12

Safety Outcomes

There were 34 patients (10%) with a thrombotic event during the 30-day follow-up period (Table 2). Of these patients, 11 had an event within 5 days after andexanet therapy, 11 had an event between 6 and 14 days, and 12 had an event between 15 and 30 days. Myocardial infarction occurred in 7 patients, ischemic stroke in 14, deep-vein thrombosis in 13, and pulmonary embolus in 5. There were 2 patients with infusion reactions, neither of which was severe. Antibodies to factor X or Xa developed in no patients after andexanet treatment, and no neutralizing antibodies to andexanet developed. There were 49 patients (14%) who died within 30 days after enrollment, 35 of cardiovascular causes, 12 of noncardiovascular causes, and 2 of unknown causes.

Reinitiation of Anticoagulation and Thrombotic Events

Factor Xa inhibitor therapy was immediately stopped in all patients at the time of enrollment. In the 30 days after andexanet treatment, 220 patients (62%) these patients, 8 (2%) had a thrombotic event after restarting anticoagulation. Of the 220 patients, 100 (28%) were restarted on oral anticoagulation during follow-up. No thrombotic events occurred after oral anticoagulation had been restarted (Table 2).

TABLE 2

Timing of thrombotic events and re-starting of anticoagulation

| Variable | Total | Safety Population (N = 352) Number of patients (percent) | | |
| --- | --- | --- | --- | --- |
| | | <6 Days after Bolus | 6-14 Days after Bolus | 15-30 Days after Bolus |
| ≥1 Thrombotic event within 30 days† | 34 (10) | 11 | 11 | 12 |
| Myocardial infarction | 7 | 6 | 1 | 0 |
| Ischemic stroke or stroke of uncertain classification | 14 | 5 | 6 | 3 |
| Transient ischemic attack | 1 | 0 | 0 | 1 |
| Deep-vein thrombosis | 13 | 1 | 5 | 7 |
| Pulmonary embolism | 5 | 1 | 0 | 4 |
| Death within 30 days‡ | 49 (14) | 8 | 21 | 20 |
| Cardiovascular cause | 35 | 7 | 15 | 13 |
| Noncardiovascular cause | 12 | 1 | 5 | 6 |
| Uncertain cause | 2 | 0 | 1 | 1 |
| Restart of any anticoagulation§ | 220 (62) | 145 (41) | 46 (13) | 29 (8) |
| Thrombotic event before restart¶ | 26 (7) | | | |
| Thrombotic event after restart | 8 (2) | | | |
| Restart of oral anticoagulation‖ | 100 (28) | 31 (10) | 37 (11) | 32 (9) |
| Thrombotic event before restart¶ | 34 (10) | | | |
| Thrombotic event after restart | 0 | | | |

*Thrombotic events that occurred on the day of restarting anticoagulation were considered to have occurred before the restart.
†Some patients had more than one thrombotic event.
‡Two deaths occurred during study follow-up, but after 30 days.
§Restart of any anticoagulation includes the use of any form of heparin or low-molecular-weight heparin, fondaparinux, or argatroban, or any oral anticoagulant, including vitamin K antagonists and non-vitamin K antagonists (at any dose and for any duration).
¶Included are thrombotic events that occurred in patients who never restarted anticoagulation.
‖Restart of oral anticoagulation includes only the use of vitamin K antagonists or non-vitamin K oral anticoagulants (at any dose and for any duration).

hours, as assessed by the independent adjudication committee on the basis of prespecified criteria. The size of the red squares is proportional to the number of patients included in the subgroup analysis. The study hypothesis was that the rate of excellent or good hemostatic efficacy would exceed 50% (indicated by the vertical dashed line). There were five patients in the efficacy population in whom hemostatic efficacy could not be adjudicated owing to administrative reasons. The four patients in the efficacy population who received edoxaban are not shown for the subgroup according to drug.

Biomarker-Efficacy Correlation

Figure 3:
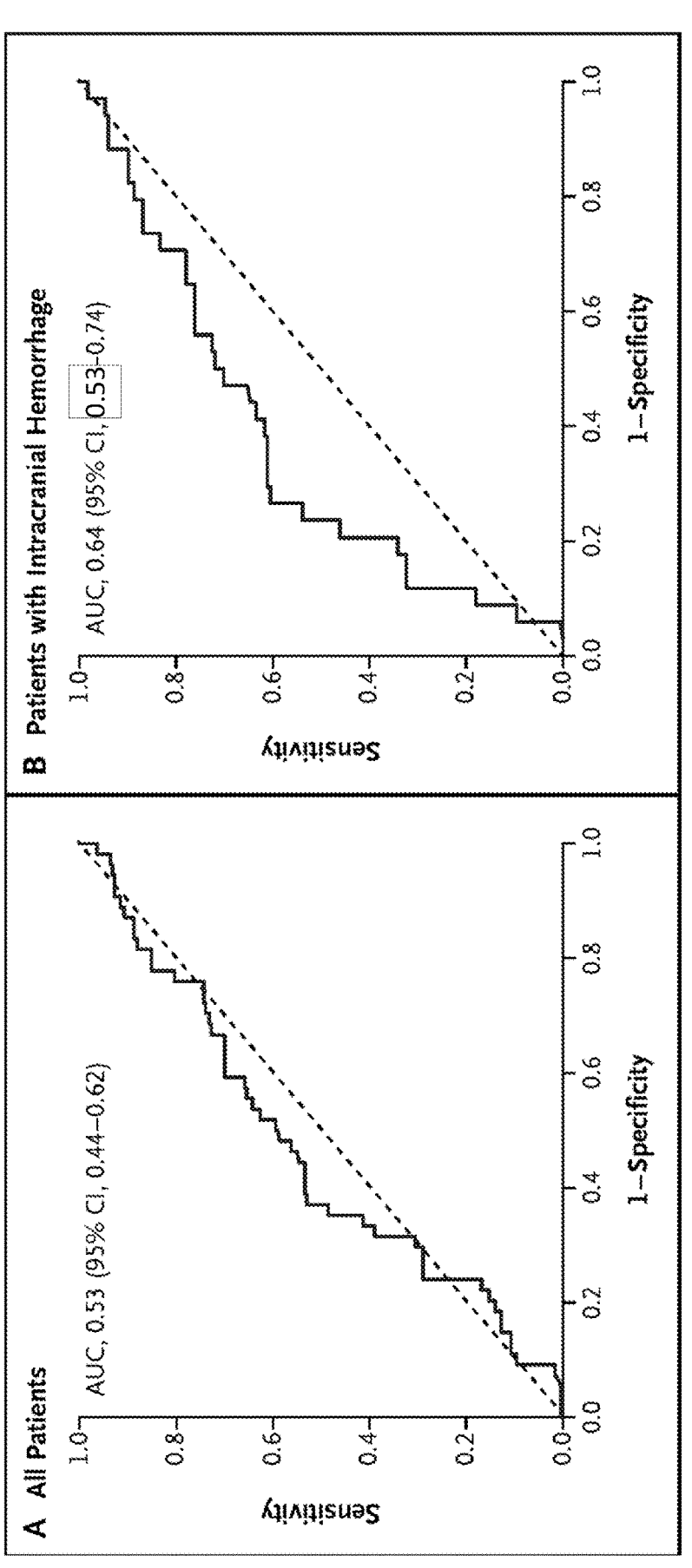
FIG. 3 presents receiver-operator characteristic curves for change in anti-factor Xa activity (ng/ml) and hemostatic efficacy (good/excellent versus poor/none) for all patients on left and for intracranial hemorrhage patients on the right.

The relationship between a change in anti-factor Xa activity during andexanet therapy and adjudicated hemostatic efficacy was evaluated by means of ROC curves. Overall, there was no significant relationship between hemostatic efficacy and a reduction in anti-factor Xa activity during andexanet treatments (FIG. 3). For patients with intracranial hemorrhage, the magnitude of the reduction in anti-factor Xa activity from baseline to nadir during treatment was a predictor of hemostatic efficacy, with an area under the ROC curve of 0.64 (95% CI, 0.54 to 0.74).

For patients with intracranial hemorrhage, however, the magnitude of the reduction in anti-factor Xa activity from baseline to nadir during treatment was a predictor of hemostatic efficacy, with an area under the ROC curve of 0.64 (95% CI, 0.54 to 0.74) (FIG. 3).

FIG. 3 presents receiver-operator characteristic curves for the association between anti-factor Xa activity (measured in nanograms per milliliter) and hemostatic efficacy (excellent or good vs. poor or none) in all patients who were receiving an oral factor Xa inhibitor (Panel A) and in patients with intracranial hemorrhage who were receiving an oral factor Xa inhibitor (Panel B). Patients are included in the analysis if assessment of hemostatic efficacy was available and if the level of anti-factor Xa activity was available at baseline and during andexanet treatment (at the end of administration of either the bolus or the infusion). The dashed line is a reference line indicating chance prediction. AUC denotes area under the curve.

Although reversal of anticoagulation is only one of several clinical factors that determine hemostatic efficacy, it was hypothesized that reduction in anti-factor Xa activity might be a predictor of clinical response. However, in the overall population, this was not the case, perhaps due to confounding by variation in bleeding source (venous, arterial), in platelet function, in type of factor Xa inhibitor and in other patient characteristics. The correlation between anti-factor Xa activity and hemostatic efficacy and clinical response may be useful for clinical response monitoring.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein. Other embodiments are within the following claims. In addition, where features or aspects of the disclosure are described in terms of Markush groups, those skilled in the art will recognize that the disclosure is also thereby described in terms of any individual member or subgroup of members of the Markush group.

---

The invention claimed is:

1. A method for treating intracranial hemorrhage, comprising:
- administering andexanet alfa to a patient undergoing an anticoagulation treatment with a factor Xa (fXa) inhibitor who has suffered intracranial hemorrhage;
- obtaining a blood sample from the patient following the administration;
- measuring an anti-fXa activity in the sample; and
- administering to the patient a second dose of the andexanet alfa if the anti-fXa activity is above a predetermined anti-fXa activity threshold,
- wherein the method does not comprise measuring hemostatic efficacy in the patient.

2. The method of claim 1, wherein the predetermined anti-fXa activity threshold is from 30 to 50 ng/ml when the fXa inhibitor is apixaban, rivaroxaban, betrixaban or edoxaban, or from 0.25 to 0.5 IU/ml when the fXa inhibitor is enoxaparin.

3. The method of claim 1, further comprising measuring the anti-fXa activity in a sample obtained from the patient prior to the administration of the andexanet alfa.

4. The method of claim 1, wherein the administration comprises a bolus injection of the andexanet alfa.

5. The method of claim 4, wherein the administration further comprises an infusion of the andexanet alfa after the bolus injection.

6. The method of claim 5, wherein the blood sample is obtained at 10 minutes to 4 hours following the administration.

7. The method of claim 1, wherein the anti-fXa activity is measured with a chromogenic assay.

* * * * *

SEQUENCE LISTING

```
<160> NUMBER OF SEQ ID NOS: 4

<210> SEQ ID NO 1
<211> LENGTH: 393
<212> TYPE: PRT
<213> ORGANISM: Artificial Sequence
<220> FEATURE:
<223> OTHER INFORMATION: Synthetic

<400> SEQUENCE: 1

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
                20                  25                  30

Asp Ser Asp Lys Thr Asn Glu Phe Trp Asn Lys Tyr Lys Asp Gly Asp
            35                  40                  45

Gln Cys Glu Thr Ser Pro Cys Gln Asn Gln Gly Lys Cys Lys Asp Gly
        50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Ile Val Gly Gly Gln
    130                 135                 140

Glu Cys Lys Asp Gly Glu Cys Pro Trp Gln Ala Leu Leu Ile Asn Glu
145                 150                 155                 160

Glu Asn Glu Gly Phe Cys Gly Gly Thr Ile Leu Ser Glu Phe Tyr Ile
                165                 170                 175

Leu Thr Ala Ala His Cys Leu Tyr Gln Ala Lys Arg Phe Lys Val Arg
```

```
                 180              185              190
Val Gly Asp Arg Asn Thr Glu Gln Glu Glu Gly Gly Glu Ala Val His
         195              200              205
Glu Val Glu Val Val Ile Lys His Asn Arg Phe Thr Lys Glu Thr Tyr
     210              215              220
Asp Phe Asp Ile Ala Val Leu Arg Leu Lys Thr Pro Ile Thr Phe Arg
225              230              235              240
Met Asn Val Ala Pro Ala Cys Leu Pro Glu Arg Asp Trp Ala Glu Ser
             245              250              255
Thr Leu Met Thr Gln Lys Thr Gly Ile Val Ser Gly Phe Gly Arg Thr
             260              265              270
His Glu Lys Gly Arg Gln Ser Thr Arg Leu Lys Met Leu Glu Val Pro
         275              280              285
Tyr Val Asp Arg Asn Ser Cys Lys Leu Ser Ser Ser Phe Ile Ile Thr
     290              295              300
Gln Asn Met Phe Cys Ala Gly Tyr Asp Thr Lys Gln Glu Asp Ala Cys
305              310              315              320
Gln Gly Asp Ala Gly Gly Pro His Val Thr Arg Phe Lys Asp Thr Tyr
             325              330              335
Phe Val Thr Gly Ile Val Ser Trp Gly Glu Gly Cys Ala Arg Lys Gly
             340              345              350
Lys Tyr Gly Ile Tyr Thr Lys Val Thr Ala Phe Leu Lys Trp Ile Asp
         355              360              365
Arg Ser Met Lys Thr Arg Gly Leu Pro Lys Ala Lys Ser His Ala Pro
     370              375              380
Glu Val Ile Thr Ser Ser Pro Leu Lys
385              390
```

<210> SEQ ID NO 2
<211> LENGTH: 359
<212> TYPE: PRT
<213> ORGANISM: Artificial Sequence
<220> FEATURE:
<223> OTHER INFORMATION: Synthetic

<400> SEQUENCE: 2

```
Ala Asn Ser Phe Leu Phe Trp Asn Lys Tyr Lys Asp Gly Asp Gln Cys
1               5               10               15
Glu Thr Ser Pro Cys Gln Asn Gln Gly Lys Cys Lys Asp Gly Leu Gly
             20               25               30
Glu Tyr Thr Cys Thr Cys Leu Glu Gly Phe Glu Gly Lys Asn Cys Glu
         35               40               45
Leu Phe Thr Arg Lys Leu Cys Ser Leu Asp Asn Gly Asp Cys Asp Gln
     50               55               60
Phe Cys His Glu Glu Gln Asn Ser Val Val Cys Ser Cys Ala Arg Gly
65               70               75               80
Tyr Thr Leu Ala Asp Asn Gly Lys Ala Cys Ile Pro Thr Gly Pro Tyr
             85               90               95
Pro Cys Gly Lys Gln Thr Leu Glu Arg Ile Val Gly Gly Gln Glu Cys
             100              105              110
Lys Asp Gly Glu Cys Pro Trp Gln Ala Leu Leu Ile Asn Glu Glu Asn
         115              120              125
Glu Gly Phe Cys Gly Gly Thr Ile Leu Ser Glu Phe Tyr Ile Leu Thr
         130              135              140
Ala Ala His Cys Leu Tyr Gln Ala Lys Arg Phe Lys Val Arg Val Gly
```

```
145              150              155              160

Asp Arg Asn Thr Glu Gln Glu Glu Gly Gly Glu Ala Val His Glu Val
             165              170              175

Glu Val Val Ile Lys His Asn Arg Phe Thr Lys Glu Thr Tyr Asp Phe
             180              185              190

Asp Ile Ala Val Leu Arg Leu Lys Thr Pro Ile Thr Phe Arg Met Asn
             195              200              205

Val Ala Pro Ala Cys Leu Pro Glu Arg Asp Trp Ala Glu Ser Thr Leu
             210              215              220

Met Thr Gln Lys Thr Gly Ile Val Ser Gly Phe Gly Arg Thr His Glu
225              230              235              240

Lys Gly Arg Gln Ser Thr Arg Leu Lys Met Leu Glu Val Pro Tyr Val
             245              250              255

Asp Arg Asn Ser Cys Lys Leu Ser Ser Ser Phe Ile Ile Thr Gln Asn
             260              265              270

Met Phe Cys Ala Gly Tyr Asp Thr Lys Gln Glu Asp Ala Cys Gln Gly
             275              280              285

Asp Ala Gly Gly Pro His Val Thr Arg Phe Lys Asp Thr Tyr Phe Val
             290              295              300

Thr Gly Ile Val Ser Trp Gly Glu Gly Cys Ala Arg Lys Gly Lys Tyr
305              310              315              320

Gly Ile Tyr Thr Lys Val Thr Ala Phe Leu Lys Trp Ile Asp Arg Ser
             325              330              335

Met Lys Thr Arg Gly Leu Pro Lys Ala Lys Ser His Ala Pro Glu Val
             340              345              350

Ile Thr Ser Ser Pro Leu Lys
             355
```

```
<210> SEQ ID NO 3
<211> LENGTH: 105
<212> TYPE: PRT
<213> ORGANISM: Artificial Sequence
<220> FEATURE:
<223> OTHER INFORMATION: Synthetic

<400> SEQUENCE: 3

Ala Asn Ser Phe Leu Phe Trp Asn Lys Tyr Lys Asp Gly Asp Gln Cys
1               5               10              15

Glu Thr Ser Pro Cys Gln Asn Gln Gly Lys Cys Lys Asp Gly Leu Gly
             20              25              30

Glu Tyr Thr Cys Thr Cys Leu Glu Gly Phe Glu Gly Lys Asn Cys Glu
             35              40              45

Leu Phe Thr Arg Lys Leu Cys Ser Leu Asp Asn Gly Asp Cys Asp Gln
             50              55              60

Phe Cys His Glu Glu Gln Asn Ser Val Val Cys Ser Cys Ala Arg Gly
65              70              75              80

Tyr Thr Leu Ala Asp Asn Gly Lys Ala Cys Ile Pro Thr Gly Pro Tyr
             85              90              95

Pro Cys Gly Lys Gln Thr Leu Glu Arg
             100              105
```

```
<210> SEQ ID NO 4
<211> LENGTH: 254
<212> TYPE: PRT
<213> ORGANISM: Artificial Sequence
<220> FEATURE:
<223> OTHER INFORMATION: Synthetic
```

```
                                    -continued

<400> SEQUENCE: 4

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
                100                 105                 110

Asp Trp Ala Glu Ser Thr Leu Met Thr Gln Lys Thr Gly Ile Val Ser
            115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
            195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250
```